United States Patent [19]

Aoki et al.

[11] 4,398,944
[45] Aug. 16, 1983

[54] HERBICIDAL COMPOSITION AND METHOD FOR INHIBITING GROWTH OF WEEDS

[75] Inventors: Katsumichi Aoki; Hideo Arabori; Keigo Satake; Hiroyasu Shinkawa, all of Iwaki, Japan

[73] Assignee: Kureha Kagaku Kogyo Kabushiki Kaisha, Tokyo, Japan

[21] Appl. No.: 273,313

[22] Filed: Jun. 15, 1981

[30] Foreign Application Priority Data

Jun. 26, 1980 [JP] Japan ............................ 55-78135

[51] Int. Cl.$^3$ ............................... A01N 37/18
[52] U.S. Cl. ............................ 71/118; 564/213
[58] Field of Search .................. 71/118; 564/213

[56] References Cited

U.S. PATENT DOCUMENTS

| | | | |
|---|---|---|---|
| 2,864,679 | 12/1958 | Hamm et al. | 71/118 |
| 3,007,786 | 11/1961 | Hamm et al. | 71/118 |
| 3,133,808 | 5/1964 | Hamm | 71/118 |
| 3,277,107 | 10/1966 | Neighbors | 71/118 |
| 3,328,156 | 6/1967 | Hopkins | 71/118 |
| 4,270,002 | 5/1981 | Kirino et al. | 71/118 |
| 4,288,244 | 9/1981 | Kirino et al. | 71/118 |

FOREIGN PATENT DOCUMENTS 1363964  5/1964  France ............................ 71/118

OTHER PUBLICATIONS

Hofstetter et al., "β-Alkylaminobutyric acid, etc.," (1953) CA49, p. 6827c (1955).
Ikeda et al., "Photochemical Synthesis, etc.;" (1976), Tetrahedron 33, pp. 489–495 (1977).

Primary Examiner—Glennon H. Hollrah
Attorney, Agent, or Firm—Wegner & Bretschneider

[57] ABSTRACT

A herbicidal composition comprising a herbicidally effective amount of a compound of the formula

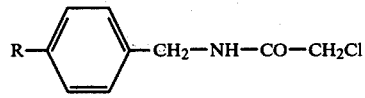

wherein R is methoxy, ethoxy, propoxy, isopropoxy or allyloxy and an agriculturally acceptable carrier and a method for inhibiting growth of weeds comprising applying the herbicidal composition to soil medium to inhibit the growth of weeds is disclosed.

6 Claims, No Drawings

HERBICIDAL COMPOSITION AND METHOD FOR INHIBITING GROWTH OF WEEDS

BACKGROUND AND DETAILED DESCRIPTION OF THE INVENTION

This invention relates to herbicidal compositions and methods for their use.

Many derivatives of 2-chloroacetamide have hitherto been synthesized and among them, several derivatives, for instance, N-benzyl-2-chloroacetamide (refer to U.S. Pat. No. 2,864,679) and N,N-diallyl-2-chloroacetamide (refer to U.S. Pat. No. 2,864,683), have been known to exhibit herbicidal activity. However, the hitherto known derivatives of 2-chloroacetamide have demerits of their insufficient effect of herbicidal action, their lack of selectivity in only controlling noxious plants or weeds and their irritating action on human skin when applied.

The present inventors, as a result of studying the herbicidal action of derivatives of 2-chloroacetamide, have found that the compounds represented by the formula

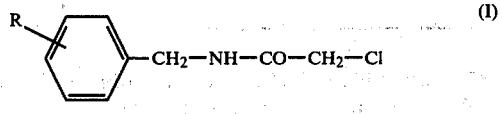
(I)

wherein R represents a methoxy, ethoxy, propoxy, isopropoxy or allyloxy have excellent herbicidal properties.

It is an object of this invention to provide a herbicidal composition comprising a herbicidally effective amount of a compound of the formula

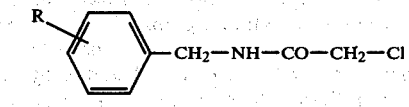

wherein R is methoxy, ethoxy, propoxy, isopropoxy or allyloxy
and an agriculturally acceptable carrier.

A further object of this invention is to provide a method for inhibiting growth of weeds comprising applying a herbicidally effective amount of a compound of the formula

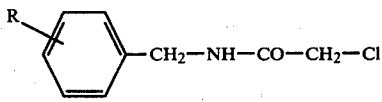

wherein R is methoxy, ethoxy, propoxy, isopropoxy or allyloxy
to soil medium to be inhibited said growth of weeds.

When applied to the fields of broad leaf crops such as cotton plants and soybean plants or the fields of other crop plants such as rice, wheat, barley and maize, these compounds exhibit excellent herbicidal activity to the graminaceous noxious weeds such as *Digitaria sanguinalis* (L.) Scopoli, *Setaria viridis* (L.) P. Beauv. var. *minor*, *Poa annua* L., *Echinochloa Crus-galli* P. Beauv. var. *hispidula* Honda, *Echinochloa Crus-galli* P. Beauve. and the likes, and to the portulacaceous noxious weeds such as *Portulaca oleracea* L. before germination or in the early stage of sprouting of the weeds into the soil of the fields.

The range of application of the compound as a component of the herbicidal composition includes the crop fields, the flooded paddy fields, orchards and non-arable fields such as play grounds and sites for factories and the like.

In addition, as a specific property of the compounds according to this invention, they do not show the irritative action to human skin in the cases where the human skin comes in contact with the compound when it is applied.

The compounds represented by the formula (I) are available by a public known process in which alkoxybenzene or allyloxybenzene is chloromethylated to chloromethylalkoxybenzene or chloromethyl-allyloxybenzene, and the thus obtained intermediate is subjected to amination to alkoxybenzylamine or allyloxybenzylamine, followed by the reaction of the aminated compound with chloroacetyl chloride. However, according to the studies of the present inventors, it has been found that the compound can be obtained simply in a high yield by amidomethylation of alkoxybenzene or allyloxybenzene with N-hydroxymethyl-2-chloroacetamide.

The concrete examples of the compounds represented by the general formula (I) and their respective structural formula are shown in Table 1.

TABLE 1

| Number of compound | Structural formula of the compound | Name of the compound | Melting point (°C.) |
|---|---|---|---|
| 1 |  | N—(2-methoxyphenyl-methyl)-2-chloroacetamide | 72–74.5 |
| 2 |  | N—(3-methoxyphenyl-methyl)-2-chloroacetamide | 78–80 |
| 3 |  | N—(4-methoxyphenyl-methyl)-2-chloroacetamide | 101–102 |

TABLE 1-continued

| Number of compound | Structural formula of the compound | Name of the compound | Melting point (°C.) |
|---|---|---|---|
| 4 | ClCH$_2$CONHCH$_2$—⟨phenyl⟩—OC$_2$H$_5$ (ortho) | N—(2-ethoxyphenyl-methyl)-2-chloroacetamide | 56–59 |
| 5 | ClCH$_2$CONHCH$_2$—⟨phenyl⟩—OC$_2$H$_5$ | N—(4-ethoxyphenyl-methyl)-2-chloroacetamide | 107–110 |
| 6 | ClCH$_2$CONHCH$_2$—⟨phenyl⟩—OC$_3$H$_7$ | N—(4-propoxyphenyl-methyl)-2-chloroacetamide | 109–110 |
| 7 | ClCH$_2$CONHCH$_2$—⟨phenyl⟩—OCH(CH$_3$)$_2$ | N—(4-isopropoxyphenyl-methyl)-2-chloroacetamide | 62–64 |
| 8 | ClCH$_2$CONHCH$_2$—⟨phenyl⟩—OCH$_2$CH=CH$_2$ | N—(4-allyloxyphenyl-methyl)-2-chloroacetamide | 109–111 |

In the cases where the compound represented by the formula (I) according to this invention may be used as a herbicidal chemical, the compound is used singly or after diluting with a diluent in the same manner as in a conventional agricultural chemical to a suitable concentration applied by scattering or spraying, and if necessary, after addition of a suitable adjuvant such as a spreading agent, a wetting agent, a sticking agent, etc. to the compound, the mixture thus obtained is naturally applied.

In addition, in the cases where the decomposition of the compound is not considered after admixing with other physiologically active chemical and there is no fear of decomposing or degrading the admixed compound, there is an advantage of combination with the other physiologically active chemicals, for instance, herbicides, plant growth regulators, fungicides, bactericides, insecticides, etc. or with fertilizers, combination meaning the parallel application and the use as a mixture with such chemicals.

Examples of synthetic processes of the compounds used as the active ingredient in this invention are shown as follows:

SYNTHETIC EXAMPLE 1

Synthesis of N-(4-methoxyphenylmethyl)-2-chloroacetamide (Compound No. 3 in Table 1)

Into an ice-cooled mixture of 80 ml of acetic acid and 20 ml of 95% sulfuric acid, 16 g of anisol and 12.4 g of N-hydroxymethyl-2-chloroacetamide (refer to Beilsteins, Handbuch der Organischen Chemie, Vol. 2, 200) were added under agitation, and after stirring the reaction mixture for 30 min, it was left stand still for 2 days. Then, the reaction mixture was poured into iced water and the thus deposited white crystals were collected by filtration. The crystals were recrystallized from an aqueous ethyl alcoholic solution to obtain 8.7 g of the object product in a yield of 41%. The product melted at 101°–102° C., and showed infrared absorption peaks at 3320 cm$^{-1}$ (due to NH), 1640 cm$^{-1}$ (due to C=O) and 1260 cm$^{-1}$ (due to —O—), respectively.

Some examples of the herbicidal composition according to this invention are shown as follows, the carrier (diluent), the adjuvant and their ratios to the active ingredient being variable in a broad range.

EXAMPLE 1

A Wettable Powder

Fifty parts by weight of Compound No. 5 in Table 1, 5 parts by weight of sodium ligninsulfonate, 3 parts by weight of sodium alkylsulfonate and 42 parts by weight of diatomaceous earth were mixed and subjected to pulverization followed by sifting to be a wettable powder of a herbicidal composition. The thus prepared wettable powder is applied after diluting with water.

EXAMPLE 2

An Emulsifiable Concentrate

Twenty five parts by weight of Compound No. 7 in Table 1, 65 parts by weight of xylene and 10 parts by weight of polyoxyethylene alkyl allyl ether were mixed together in a homogenizer to an emulsifiable concentrate. The thus prepared emulsifiable concentrate is applied after diluting with water.

EXAMPLE 3

Herbicidal Granular Composition

Eight parts by weight of Compound No. 7 in Table 1, 40 parts by weight of bentonite, 45 parts by weight of clay and 7 parts by weight of sodium ligninsulfonate were uniformly mixed, and after adding water to the mixture, the muddy mixture was kneaded well and extruded from a kneading and shaping machine as wet granules. The thus extruded granules were dried to be a herbicidal granular composition.

In order to show the effectiveness of the compound according to this invention, some examples of herbicidal test experiments are shown below.

TEST EXAMPLE 1

Herbicidal effect of soil treatment with the herbicidal composition before germination of weeds in upland field In a planter of dimensions of 650×210×200 mm filled with soil to be a state of upland field, a predetermined amount of the seed of respective crops of maize, soybean, cotton and wheat, and of respective weeds of *Echinochloa Crus-galli* P. Beauv. *Digitaria sanguinalis* (L.) Scopoli, *Setaria viridis* (L.) P. Beauv. var. *minor*, *Poa annua* L., *Cyperus microiria* Steudel, *Portulaca oleracea* L., *Chenopodium album* L., *Polygonum lapathifolium* L. subsp. *nodosum* and *Cardamine flexuosa* With. were scattered on the surface of the soil thereof, and after covering the seeds lightly with the soil, an amount of respective diluted aqueous suspension of the compound was sprayed on the surface of the soil uniformly so that the amount of the compound per one are of the surface of the soil was 50 g. The thus treated planters were kept on a greenhouse under the conventional conditions of growing plants.

On the 25th day of the treatment, the herbicidal effects and the phytotoxicity to the crop plants were investigated and the records were arranged according to the following standards of evaluation. The results were shown in Table 2.

Standards of evaluation:

| Mark: Herbicidal effect | Mark: Phytotoxicity to crop plants |
|---|---|
| 0: no effect | −: no injury |
| 1: 20% kill | ±: a slight injury |
| 2: 40% kill | +: a relatively slight injury |
| 3: 60% kill | ++: a moderate injury |
| 4: 80% kill | +++: a severe injury |
| 5: 100% kill | ++++: withered |

TABLE 2

Herbicidal Effect and Phytotoxicity to Crop Plants

| Number of com- pound | Herbicidal effect Name of weeds (refer to Note) | | | | | | | | | Phytotoxicity to Crop Plant Crop Plants (refer to Note) | | | |
|---|---|---|---|---|---|---|---|---|---|---|---|---|---|
| | A | B | C | D | E | F | G | H | I | 1 | 2 | 3 | 4 |
| 1 | 4 | 4 | 3 | 4 | 5 | 2 | 3 | 2 | 3 | − | − | − | − |
| 3 | 5 | 5 | 5 | 5 | 5 | 4 | 4 | 4 | 3 | − | + | − | + |
| 5 | 5 | 5 | 5 | 5 | 5 | 4 | 5 | 4 | 2 | − | − | − | + |
| 7 | 5 | 5 | 4 | 5 | 5 | 1 | 4 | 3 | 2 | − | + | − | − |
| 8 | 5 | 5 | 5 | 4 | 5 | 4 | 4 | 1 | 1 | − | − | − | − |
| Comparative herbicide | 4 | 4 | 2 | 3 | 1 | 1 | 1 | 1 | 0 | − | − | − | + |
| Non-treatment | 0 | 0 | 0 | 0 | 0 | 0 | 0 | 0 | 0 | − | − | − | − |

TABLE 2-continued

Herbicidal Effect and Phytotoxicity to Crop Plants

| Number of com- pound | Herbicidal effect Name of weeds (refer to Note) | | | | | | | | | Phytotoxicity to Crop Plant Crop Plants (refer to Note) | | | |
|---|---|---|---|---|---|---|---|---|---|---|---|---|---|
| | A | B | C | D | E | F | G | H | I | 1 | 2 | 3 | 4 |

Notes:
Weed No. A: *Echinochloa Crus-galli* P. Beauv.
Weed No. B: *Digitaria sanguinalis* (L.) Scopoli
Weed No. C: *Setaria viridis* (L.) P. Beauv. var. minor
Weed No. D: *Poa annua* L.
Weed No. E: *Cyperus microiria* Steudel
Weed No. F: *Portulaca oleracea* L.
Weed No. G: *Chenopodium album* L.
Weed No. H: *Polygonum lapathifolium* L. subsp. nodosum
Weed No. I: *Cardamine flexuosa* With.
Crop Plants No. 1: maize
Crop Plants No. 2: soybean plant
Crop Plants No. 3: cotton plant
Crop Plants No. 4: wheat
Comparative herbicide:

⟨◯⟩—$CH_2$—NH—CO—$CH_2$—Cl (N—benzyl-2-chloroacetamide disclosed in U.S. Pat. No. 2,864,679)

TEST EXAMPLE 2

Herbicidal effect of treating the weeds at their sprouting stage with the herbicidal composition In a similar planter filled with the same kind of the soil as in Test Example 1, the same seeds of the weeds and crop plants were sown, and at the time when the crop plants and weeds became in the one to two leaves state, an aqueous suspension of the herbicide was sprayed onto the aerial parts of all the plants and the surface of the soil uniformly and the planter was kept in a greenhouse under the same conditions as in Test Example 1, the concentration of the herbicidal composition in the aqueous suspension being adjusted so that the amount of the compound as an effective ingredient sprayed on the unit surface area of one are was 50 g. The results were investigated on 25th day of the treatment, and shown in Table 3 while using the same standard of evaluation as in Test Example 1.

TABLE 3

| Number of com- pound | Herbicidal effect Name of weeds (same as Test Ex. 1) | | | | | | | | | Phytotoxicity to Crop Plant Crop plants (same as Test Ex. 1) | | | |
|---|---|---|---|---|---|---|---|---|---|---|---|---|---|
| | A | B | C | D | E | F | G | H | I | 1 | 2 | 3 | 4 |
| 1 | 4 | 4 | 3 | 3 | 5 | 3 | 2 | 1 | 3 | − | − | − | − |
| 3 | 5 | 5 | 5 | 5 | 4 | 4 | 3 | 3 | 2 | ± | + | − | + |
| 4 | 4 | 2 | 2 | 4 | 5 | 1 | 2 | 1 | 2 | − | − | − | − |
| 5 | 5 | 5 | 5 | 5 | 5 | 4 | 4 | 3 | 2 | ± | + | − | + |
| 7 | 5 | 5 | 4 | 5 | 5 | 1 | 4 | 3 | 1 | ± | + | − | − |
| 8 | 5 | 4 | 5 | 5 | 5 | 4 | 3 | 1 | 0 | − | − | − | − |
| Comparative herbicide | 4 | 4 | 4 | 4 | 1 | 2 | 0 | 0 | 0 | − | − | − | + |
| Non-treatment | 0 | 0 | 0 | 0 | 0 | 0 | 0 | 0 | 0 | − | − | − | − |

TEST EXAMPLE 3

Herbicidal test on the weeds in simulated flooded paddy field

In pots of 1/5000 with the soil in a state of flooded paddy field, the two species of weeds, *Echinochloa*

*Crus-galli* and *Cyperus microiria* were grown respectively at their states of three leaves, of two leaves and of just before emergence. An aqueous suspension of the candidate herbicidal compositions was injected onto the surface of water in the pots in an amount of the compound corresponding to 15 g/are of the surface area of the pot.

After 3 days of the injection, the seedlings of rice plant in a stage of 2.5 leaves were transplanted to the pots, and the herbicidal effect and phytotoxicity were investigated according to the same standards of evaluation as in Test Example 1. The results are shown in Table 4.

TABLE 4

Test Results in Flooded Paddy Field (simulated)

| Number of compound | Herbicidal Effect | | | | Phytotoxicity to Rice Plant |
|---|---|---|---|---|---|
| | Weed No. A | | Weed No. E | | |
| | α | γ | β | γ | |
| 1 | 4 | 5 | 4 | 5 | — |
| 2 | 3 | 5 | 3 | 4 | — |
| 3 | 5 | 5 | 4 | 5 | — |
| 4 | 4 | 5 | 4 | 4 | — |
| 5 | 5 | 5 | 5 | 5 | + |
| 6 | 3 | 5 | 4 | 4 | — |
| 7 | 5 | 5 | 5 | 5 | + |
| 8 | 5 | 5 | 4 | 5 | + |
| Comparative herbicide | 2 | 2 | 2 | 2 | ± |
| Non-treatment | 0 | 0 | 0 | 0 | — |

TABLE 4-continued

Test Results in Flooded Paddy Field (simulated)

| Number of compound | Herbicidal Effect | | | | Phytotoxicity to Rice Plant |
|---|---|---|---|---|---|
| | Weed No. A | | Weed No. E | | |
| | α | γ | β | γ | |

Notes:
α means those in three leaves stage
β means those in two leaves stage
γ means those just before emergence

What is claimed is:

1. A method for inhibiting growth of weeds comprising applying a herbicidally effective amount of a compound of the formula:

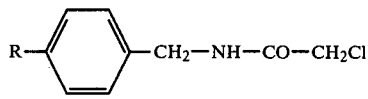

wherein R is a methoxy-, ethoxy-, propoxy-, isopropoxy- or allyloxy to soil to inhibit the growth of weeds.

2. The method according to claim 1, wherein said compound is N-(4-methoxyphenylmethyl)-2-chloroacetamide.

3. The method according to claim 1, wherein said compound is N-(4-ethoxyphenylmethyl)-2-chloroacetamide.

4. The method according to claim 1, wherein said compound is N-(4-propoxyphenylmethyl)-2-chloroacetamide.

5. The method according to claim 1, wherein said compound is N-(4-isopropoxyphenylmethyl)-2-chloroacetamide.

6. The method according to claim 1, wherein said compound is N-(4-allyloxyphenylmethyl)-2-chloroacetamide.

* * * * *